United States Patent [19]
Ruiz

[11] Patent Number: 5,928,129
[45] Date of Patent: *Jul. 27, 1999

[54] APPARATUS AND METHOD FOR PERFORMING PRESBYOPIA CORRECTIVE SURGERY

[76] Inventor: Luis Antonio Ruiz, Carrera 9$^a$ No. 83-15, 4th Floor, Santafè de Bogotá, Colombia

[*] Notice: This patent is subject to a terminal disclaimer.

[21] Appl. No.: 08/660,376

[22] Filed: Jun. 7, 1996

Related U.S. Application Data

[63] Continuation-in-part of application No. 08/268,182, Jun. 29, 1994, Pat. No. 5,533,997.

[51] Int. Cl.$^6$ .................................................. A61N 5/06
[52] U.S. Cl. ..................................................... 600/5; 600/4
[58] Field of Search ............................... 606/4, 5, 6, 10, 606/11, 12, 13, 166

[56] References Cited

U.S. PATENT DOCUMENTS

| | | |
|---|---|---|
| 4,173,980 | 11/1979 | Curtin . |
| 4,461,294 | 7/1984 | Baron . |
| 4,660,556 | 4/1987 | Swinger et al. . |
| 4,662,370 | 5/1987 | Hoffmann et al. . |
| 4,665,914 | 5/1987 | Tanne . |
| 4,674,503 | 6/1987 | Peyman et al. . |
| 4,688,570 | 8/1987 | Kramer et al. . |
| 4,705,035 | 11/1987 | Givens . |
| 4,718,418 | 1/1988 | L'Esperance, Jr. . |
| 4,729,372 | 3/1988 | L'Esperance, Jr. . |
| 4,770,172 | 9/1988 | L'Esperance, Jr. . |
| 4,773,414 | 9/1988 | L'Esperance, Jr. . |
| 4,798,204 | 1/1989 | L'Esperance, Jr. . |
| 4,840,175 | 6/1989 | Peyman . |
| 4,856,513 | 8/1989 | Muller . |
| 4,880,017 | 11/1989 | Soll . |
| 4,903,695 | 2/1990 | Warner et al. . |
| 4,907,586 | 3/1990 | Bille et al. . |
| 4,988,348 | 1/1991 | Bille . |
| 5,009,660 | 4/1991 | Clapham . |
| 5,019,074 | 5/1991 | Muller . |

(List continued on next page.)

FOREIGN PATENT DOCUMENTS

| | | |
|---|---|---|
| A-346116 | 12/1989 | European Pat. Off. . |
| A-402250 | 12/1990 | European Pat. Off. . |
| WO 94/01067 | 1/1994 | WIPO . |

OTHER PUBLICATIONS

*Lasers in Surgery and Medicine*, vol. 10, No. 5, Jan. 1, 1990, pp. 463–468, XP 000385912, Pallikaris: "Laser In–Situ Keratomileusis".

*Steinway Instrument Co.*, The Steinway/Barraquer In–Situ Microkeratome Set, from the Steinway Instrument Co. of San Diego, California.

*Primary Examiner*—Robert L. Nasser
*Attorney, Agent, or Firm*—Beveridge, DeGrandi, Weilacher & Young, LLP

[57] ABSTRACT

A process for surgically correcting presbyopia includes anesthetizing a patient and marking a portion of an eye of the patient which is to be ablated. At least a portion of the cornea is resected to expose the corneal stroma. An annular portion of the corneal stroma is then ablated using radiation from a laser beam. After ablation, the cornea is repositioned onto the eye. The cornea may be resected such that a portion of the cornea remains intact, and is folded back to expose the corneal stroma. Alternatively, a complete disk of the cornea may be removed from the eyes to thereby expose the corneal stroma. After exposure but before ablating, the corneal stroma should be dried to prevent uneven ablation which may occur if fluids are present on the stroma. The laser beam may be directed in a circular fashion until an annular ablation is formed, or a mask may be provided over a central area of the corneal stroma. To prevent edema, the ablated portion should be cleaned by brushing and irrigating. A system for surgically performing the presbyopia correction process also is described. This system includes a marker, a resector such as an automatic corneal shaper, and a laser for ablating the corneal stroma.

40 Claims, 3 Drawing Sheets

U.S. PATENT DOCUMENTS

| | | |
|---|---|---|
| 5,133,726 | 7/1992 | Ruiz et al. . |
| 5,152,759 | 10/1992 | Parel et al. . |
| 5,163,934 | 11/1992 | Munnerlyn . |
| 5,207,668 | 5/1993 | L'Esperance, Jr. . |
| 5,246,435 | 9/1993 | Bille et al. . |
| 5,263,951 | 11/1993 | Spears et al. . |
| 5,314,422 | 5/1994 | Nizzola ......... 606/5 |
| 5,324,281 | 6/1994 | Muller . |
| 5,395,356 | 3/1995 | King et al. . |
| 5,437,658 | 8/1995 | Muller et al. . |
| 5,439,462 | 8/1995 | Bille et al. . |
| 5,533,997 | 7/1996 | Ruiz ......... 606/5 |
| 5,651,784 | 7/1997 | Klopotek . |

1

APPARATUS AND METHOD FOR PERFORMING PRESBYOPIA CORRECTIVE SURGERY

REFERENCE TO A RELATED APPLICATION

This application is a continuation-in-part of my application Ser. No. 08/268,182 filed Jun. 29, 1994, now U.S. Pat. No. 5,533,997 which is relied on and incorporated herein by reference.

BACKGROUND OF THE INVENTION

The invention relates to an apparatus and method for correcting presbyopia through surgery. The system used in accordance with the invention (called a "PRESBYSYSTEM") includes several different elements that, when used together, modify the front corneal curvature, thereby creating a multifocal surface that permits the patient to see with normal vision with respect to objects at a distances while also permitting the patient to see nearby objects with normal vision. This simultaneous correction of near and distant vision is accomplished through the use of just a part of the corneal surface (the middle). This means that the portion of the corneal area which is used for near vision is not the same as that used for long distance vision.

Most people, as they age, suffer from a presbyopia problem. The usual way to correct this problem is to use bifocal lenses. However, some people dislike wearing glasses, particularly bifocals, for many reasons. Bifocal lenses present lines where the two portions of the lens are joined together. Furthermore, people must become accustomed to reading through the one relatively small portion of the lens, while looking at distant objects through a different portion of the lens. Bifocal glasses also have the disadvantages present in regular glasses. Such disadvantages include the fact that glasses are breakable, they become fogged when coming in from the cold, they steam up in hot weather, and they require periodic cleaning.

This invention is directed to an apparatus and method for correcting the presbyopia problems directly on the eye of the patient, such that the use of glasses is avoided and the eye of the patient will adapt the focus automatically for nearsight and farsight

SUMMARY OF THE INVENTION

The invention relates to a process for surgically correcting presbyopia. The process includes anesthetizing a patient and marking a portion of an eye of the patient which is to be ablated. At least a portion of the cornea is resected to expose the corneal stroma. An annular portion of the corneal stroma is then ablated using radiation from a laser beam. After ablation, the cornea is repositioned onto the eye.

In the process according to the invention, the cornea may be resected such that a portion of the cornea remains intact, and thereafter the cornea may be folded back to expose the corneal stroma. Alternatively, the cornea may be resected such that a complete disk of the cornea is removed from the eye, to thereby expose the corneal stroma. Thereafter, the cornea disk would have to be reattached onto the eye.

The corneal stroma should be dried after it has been exposed by the resection and before the ablation process. Otherwise, uneven ablation may occur due to liquids present on the stroma.

During ablation, the laser beam may be directed in a circular fashion until an annular ablation of a predetermined width and depth is provided. Alternatively, a mask may be provided over a central area of the corneal stroma to stop the radiation from the laser beam at the central portion. In this instance, the laser beam diameter is controlled (and provided somewhat larger than the mask diameter) such that an annular ablation of a predetermined width and depth is provided. The mask may be made from polymethyl methacrylate or other suitable synthetic resin. The laser may be a conventional pulsed laser.

After ablating, the ablated portion should be cleaned, in order to prevent edema. This may be accomplished by brushing and irrigating the portion which was ablated.

Once the cornea portion has been properly repositioned, it may be reattached to the eye by blowing air onto the cornea.

The invention also relates to a system for surgically correcting presbyopia. This system includes a means for marking a portion of an eye of a patient which is to be ablated. A means for resecting at least a portion of a cornea of the eye of the patient is included for the purpose of exposing the corneal stroma. The system further includes a means for ablating an annular portion of the corneal stroma. This means for ablating includes a laser (such as a pulsed laser) wherein ablation takes place by irradiating the corneal stroma with radiation from the laser.

A corneal shaper may be provided as the means for resecting, wherein the corneal shaper either partially resects the cornea such that a portion of the cornea remains intact, or fully removes a corneal disk, as mentioned above. The system may further include a means for drying the corneal stroma after it has been exposed by the means for resecting, such as by blowing air thereon.

In order to ablate the corneal stroma in an annular fashions a mask may be provided with the means for ablating for positioning over a central area of the corneal stroma to stop the radiation from the laser. This mass may be made from a material which stops laser radiation, such as polymethyl methacrylate (PMMA) or other suitable synthetic resin. A means for providing a predetermined diameter to a laser beam from the laser is provided with this embodiment to limit the laser beam width so that an annular ablation of a predetermined width and depth is provided.

The system in accordance with the invention is preferably provided with a means for cleaning the portion of the stroma which was ablated. This means for cleaning may include a delicate brush or a means for irrigating the portion which was ablated, or both.

BRIEF DESCRIPTION OF THE DRAWINGS

The invention will be described in more detail with the aid of the attached drawings, wherein.

DETAILED DESCRIPTION OF THE INVENTION

Figure 1:
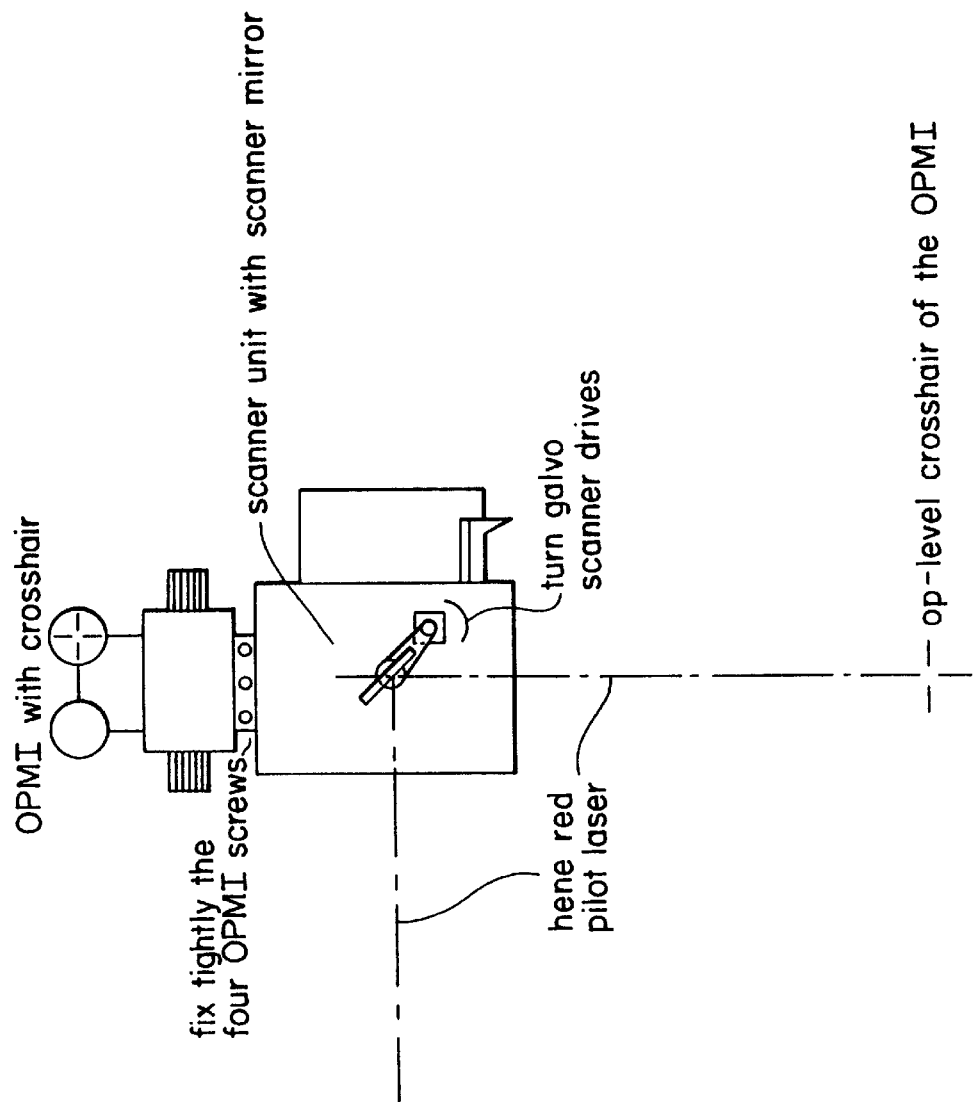
FIG. 1 is schematic view of a portion of the excimer laser where the setting of the axis of the laser ray is performed.

The system in accordance with the invention includes an excimer laser, an automatic corneal sharper, a pneumatic fixation ring, a mask and an air source. A preferred automatic corneal shaper for use in the system in accordance with this invention is the Automatic Corneal Shaper described in the inventor's U.S. Pat. No. 5,133,726, issued on Jul. 28, 1992. This patent is entirely incorporated herein by reference.

Using only a local anesthesia, the eye is fixed by the fixation ring which also functions as a guide for the automatic corneal shaper. The fixation or retaining ring, as illustrated in the above mentioned U.S. Pat. No. 5,133,726, permits total control of the eye movement. The pupil of the eye will be a reference point for making a very central stromal ablation on the cornea.

Once the eye is fixed, a keratectomy is performed using the automatic corneal shaper The keratectomy may be partial which means that a cornea flap technique is used. This means that an and portion of the corneal disc remains attached to the cornea base which thereby permits its repositioning in an easier and surer way, once the ablation is performed When the flap is retracted, the corneal stroma becomes exposed, which is ideal tissue on which to practice the ablation. The superficial layers of the cornea remain untouched. In this way undesirable healing is avoided, and inaccuracy in the post operative correction and regression is also avoided.

Using an excimer laser, which accurately allows an ablation of 0.24 $\mu$m/pulse, an annular ablation is made on the stroma having a diameter not exceeding 3.5 mm, with a central zone as small as 1 mm diameter and varying between 1 and 3 mm The annular ablation produces a central protrusion of the stroma such that when the corneal flap is repositioned at its initial position, this stromal curvature change is transmitted to the forward corneal surface, thereby transforming it into a multifocal surface, which is in fact myopic in its central part. This is what makes it possible for the patient to read without optic correction after the procedure, regardless of the age of the patient or the loss of accommodation.

The annular ablation can be made in isolated form, for presbyopia correction, or it can be made together with hyperopia, myopia and astigmatism surgery, either isolated or combined. After the ablation is made, the procedure continues with exhaustive cleaning of the interface using a balanced saline solution, a brush and aspiration, in order to assure that the interface is free from impurities, epithelial cells or foreign particles. Thereafter, the flap is replaced in the bed, adequately oriented in order to avoid altering its natural position. The edges of the flap are dried using air for several seconds to obtain adherence of the flap, such that the patient may be permitted to leave the operating room with no bandages and to obtain less than 24 hours recovery time.

The following is a more detailed description of an example of the apparatus and method for performing presbyopia correction surgery. A conventional topical anesthesia (ie., in the form of eye drops) is applied onto the patient's eye. This topical anesthesia is sufficient for the surgical technique in accordance with the invention to do a painless job. Next, a pneumatic fixation ring is positioned over the eye.

In this type of surgery, centering of the device on the eye's pupil is vital. Furthermore, it is desirable to have the pupil as small as possible. For this purpose it is convenient to apply a drop of Isopto-Carpine at a 2%, a half an hour prior to the surgery. From then on, this small pupil will be used as a reference point for making the ablation.

The surgical procedure in accordance with the invention should be carried out in a sterile area (i.e., a surgery room), because the cornea will be touched not in a superficial manner as would be required for the photo-ablation for the correction of myopia. Rather, in the presbyopia corrective surgical technique in accordance with the invention, a corneal flap is lifted in a laminar way in order to work directly on the stroma. Therefore surgical fields are located in order to isolate the working area and also a blepharostat is provided in order to maintain the eye sufficiently exposed so as to be able to practice the surgery.

A marker is advantageously used to aid in the practice of the invention. The marker used in this new technique has the shape of a bullock eye having two concentric circles (thereby forming an inner ring and an outer ring) in which its external portion has a diameter of about 10.S mm and its inner part has a diameter of about 3 to 5 mm. This marker is impregnated with a coloring product, such as gentian violet, methylene blue, or the like. The marker is placed on the patient's eye. The internal ring has the function of centering the marker, having as a reference point, the pupil. In this manner, the external ring is automatically marked and in turn this will be used as a reference when positioning of the pneumatic fixation ring. In addition to these two rings, the marker also has a para-radial line joining both rings. The para-radial lines are useful for adequately orienting the corneal flap. Alternatively, in the case where a completely separated corneal disk is removed for the surgical procedure instead of using a corneal flap, the para-radial lines are used in order to assist in positioning the disk in the right place, that is, epithelial toward the exterior and stroma toward the inner part, and once located in this manner, it may now be oriented in adequate form.

The pneumatic fixation ring comprises two main components. The ring itself which will be adapted to the eye by means of a bottom vacuum chamber allowing it in this manner to hold the eye in place and to increase the inter ocular pressure This makes it easier to make the necessary cut in the cornea in a uniform manner. The fixation ring also has a central orifice through which the cornea protrudes. In its top portion, the most important component of the fixation ring is a line of toothed protrusions which contact with the pinions of the automatic corneal shaper (see U.S. Pat. No. 5,133,726). This allows the corneal shaper to be displaced in a horizontal way for performing the laminar cut in the cornea. The second component of this ring is a handle which places the bottom vacuum chamber of the fixation ring in communication with a vacuum pump. The vacuum pump is responsible for suction fitting the ring on the patient's eye. This handle also is used to manipulate the eye once the ring is fixed to the eye.

The next step of the surgical procedure is performed by the automatic corneal shaper, as noted above. The shaper is positioned over the fixation ring, and once the pinions of the shaper are in contact with the toothed protrusions of the ring, the shaper motor is started, and the shaper is moved horizontally and uniformly over the cornea. The cutter of the shaper will make the laminar cut very accurately in its thickness, in the manner described in U.S. Pat. No. 5,133,726.

Preferably, the motor of the shaper is stopped at a predetermined position of the cut so as to have a thin portion of cornea still fixed to one side. When this thin portion is lifted, the corneal stroma will appear. The corneal stroma is the place where the object of the surgery will be practiced, because it has the great advantage that once the corneal flap is repositioned after the stromal ablation, all the natural structures of the eye will be preserved in their original place, but with a change in topography, thereby avoiding unwanted healing, and other alterations that would be present if this system is not used.

Once the exposed stromal surface is examined, it must be dried prior to the ablation action of an excimer laser, because any remaining fluid on the stroma will be considered by the laser ray as corneal tissue. This would result in an irregular ablation. That is, different depths of ablation would be produced on the stroma.

Figure 2:
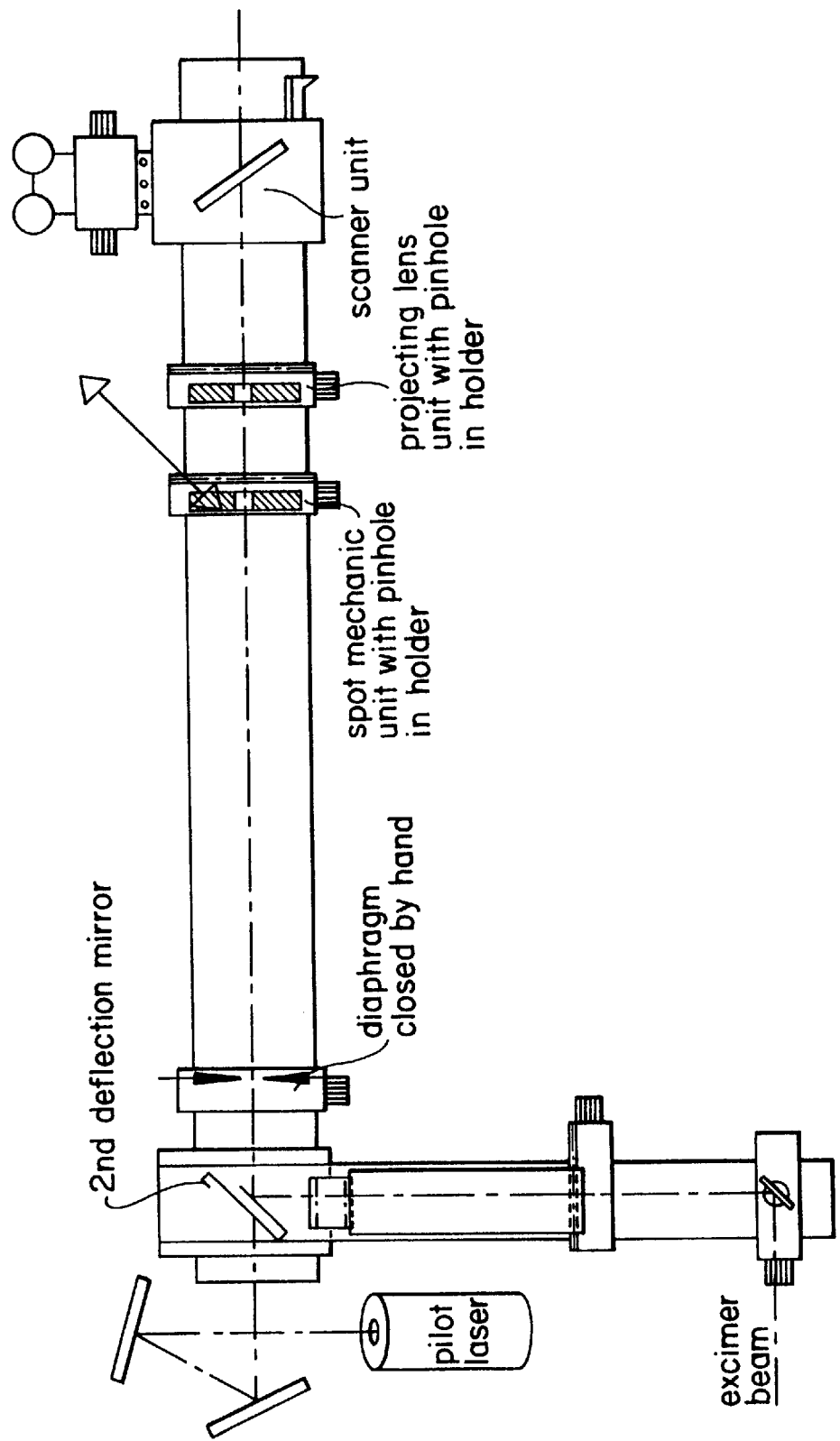
FIG. 2 is a schematic view of the path of the laser beam and the optics used in an embodiment of the apparatus according to the invention

One main element of this new system for the correction of presbyopia is the excimer laser. The excimer laser system, as illustrated in FIGS. 1 and 2, is one that will perform the correction of this visual defect by providing a stromal ablation the required manner, location and depth in order to create a multifocal surface in the cornea that allows good far sight, as well as good near sight. This sight usually is lost during a person's later years due to a physical lace of accommodation and loss of elasticity of the lens.

The system includes the novel combination of the above elements in order to obtain an annular shaped ablation within a corneal area which is not used for far sight. These are the theoretical and real bases of the system in accordance with the invention for presbyopia correction. There can be different ways to obtain the results, as will be described below.

In one embodiment, the laser is directed toward a zone where the ablation must be done The laser is directed with a circular movement of the laser beam so that the ablation is made with the required width and depth, to thereby obtain the desired change in curvature. For this, the apparatus that sands the laser ray beam includes an eye follower system in order to follow any movement of the eye, so that an irregular ablation ring does not result.

Figure 3A:
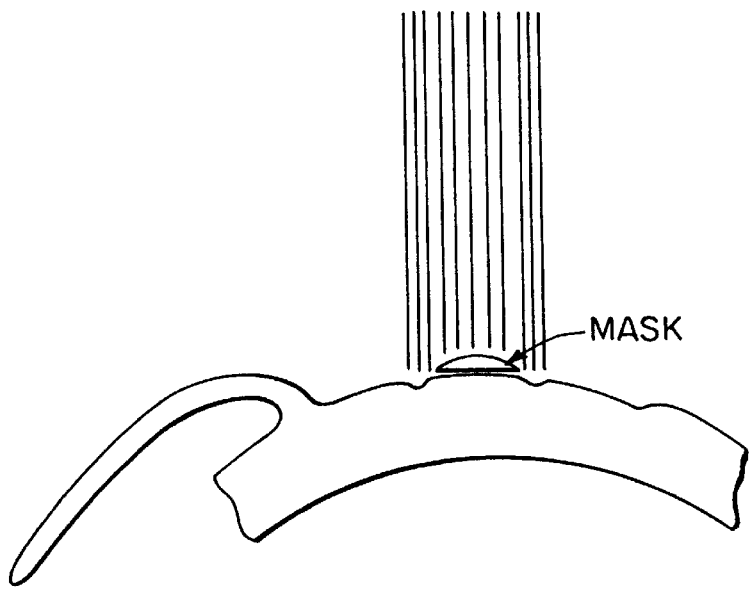
FIG. 3A shows the laser beam performing the ablation on the cornea, and the mask protecting the center area of the cornea.
Figure 3B:
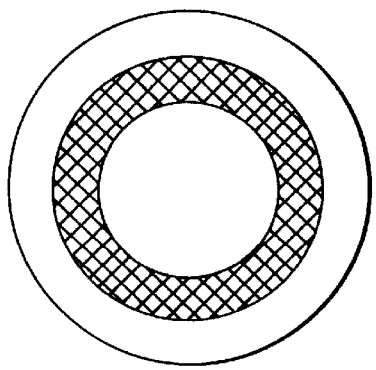
FIG. 3B shows the ring for the ablation zone.
Figure 3C:
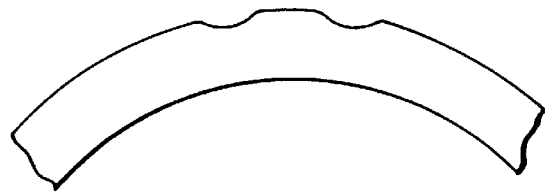
FIG. 3C shows the Way the ablation of the cornea appears finally.

In another embodiment, as shown in FIG. 3A, the laser beam ray is sent toward the center of the chosen area, having as a reference point the small pupil. A mask is positioned over the central area so that it prevents the laser rays from touching the corneal stroma in the central area. In this manner, the ablation will be delimited at the outside by the selected diameter of the laser beam and at the inside by the border of the mask, thereby leaving a ring shaped area, as shown in FIGS. 3B and 3C. Using the mask, the cornea over the pupil area will be totally preserved.

With this in mind, the surgical method for presbyopia correction proceeds in the following manners once the stroma is totally dried, the area that is not to be touched by the laser ray is marked. That area will be called the optic zone taking into account that the fundamental factor for the success of the operation lays on the centering of such optic zone. The diameter of this optic zone can be as small as 1 mm and must be between about 1 to 3 mm.

Now over the marked area, a mask is provided, made out of a material that stops the laser rays. For the mask, generally a material called polymethyl methacrylate (PMMA) is used, and it should have the same dimension of the mark already located.

The laser apparatus is then positioned so as to provide laser rays on the cornea Such laser systems are commercially available such as provided by Chiron Technolas GmbH. The laser apparatus is previously set in order to obtain a laser ray having the desired diameter. It also may be set up so as to provide a predetermined number of pulses which will be required for performing an ablation having an adequate depth so that the necessary corneal curvature change is produced, in order to obtain the multifocal effect. During the time of action of the laser ray over the cornea, and mainly when the laser equipment is not provided with an eye follower system, it is convenient to hold the eye with a pneumatic fixing ring in view of the fact that this permits a greater uniformity of the ablation ring produced.

Once the ablation step is completed, the mask is withdrawn, and the treated zone inspected and cleaned up completely, making sure that no epithelial cells or foreign particles remain on the surface. The cleaning step is normally accomplished with a very delicate brush, with continuous irrigating using a balanced saline solution having an osmolarity similar to that of the cornea. This helps to avoid the induction of an important edema therein, which would cause a longer patient recovery time.

Now the treated surface is ready to receive the flap which has to be repositioned in its place, perfectly oriented and without folds that would cause induction of corneal astigmatism and reduction of the sight Once the flap is repositioned, the tissue is dried by means of filtered air directed mainly to the borders thereof to thereby obtain a good bonding of the flap to the treated surface. This bonding may be verified or tested with tweezers.

Once the tissues are bonded, the Blepharostat and the— surgical fields are withdrawn, and the patient is asked to blink their eyes several times and to close their eyes tightly, to further test the bonding of the tissues If no complications are observed, the operation is now successfully ended.

While the invention has been described in terms of various preferred embodiments and methods for performing the procedure, those skilled in the art will recognize that various changes and modifications may be made without departing from the spirit and scope of the invention, as defined in the appended claims.

I claim:

1. A process for surgically correcting presbyopia comprising:
   anesthetizing a patient;
   resecting at least a portion of a cornea of an eye of the patient to expose a corneal stroma;
   ablating an annular portion of the corneal stroma using radiation from a laser beam wherein during the ablating step, a central optical zone of the corneal stroma with a diameter as small as 1 mm is left unablated; and
   repositioning the portion of the cornea onto the eye wherein a central corneal curvature change is induced to thereby correct presbyopia in the patient.

2. A process according to claim 1, wherein in the resecting step, the cornea is resected such that a portion of the cornea remains intact, and the cornea is folded back to expose the corneal stroma and wherein the ablating leaves the unablated central optic zone having a diameter in the range of about 1–3 millimeters.

3. A process according to claim 1, wherein in the resecting step, the cornea is resected such that a portion of the cornea remains intact, and the cornea is folded back to expose the corneal stroma.

4. A process according to claim 1, wherein in the resecting step, the cornea is resected such that a disk of the cornea is removed from the eye, to thereby expose the corneal stroma.

5. A process according to claim 1a further including drying the corneal stroma after it has been exposed in the resecting step and before the ablating step.

6. A process according to claim 1, wherein the ablating step is accomplished by directing the laser beam in a circular fashion until an annular ablation of a predetermined width and depth is provided.

7. A process according to claim 1, wherein the ablating step is accomplished by providing a mask over a central area of the corneal stroma to stop the radiation from the laser beam and providing the laser beam with a predetermined width and depth is provided.

8. A process according to claim 7, wherein the ablating step is accomplished by providing a mask made from polymethyl methacrylate over a central area of the corneal stroma to stop the radiation from the laser beam, and providing the laser beam with a predetermined diameter, such that an annular ablation of a predetermined width and depth is provided.

9. A process according to claim 1, wherein the laser is a pulsed laser.

10. A process according to claim 1, further including cleaning the portion which was ablated after the ablating step.

11. A process according to claim 10, wherein the cleaning step includes brushing and irrigating the portion which was ablated.

12. A process according to claim 1, wherein after the cornea is repositioned, drying the cornea by blowing air onto the cornea.

13. A process for surgically correcting presbyopia according to claim 1 wherein the central optic zone has a diameter in the range of about 1–3 millimeters.

14. A process for surgically correcting presbyopia according to claim 13, wherein the annular portion which is ablated has an outer diameter not exceeding 3.5 millimeters.

15. A process for surgically correcting presbyopia according to claim 1, wherein the annular portion which is ablated has an outer diameter not exceeding 3.5 millimeters.

16. A process according to claim 1 wherein the laser beam is directed against a mask which is formed of a material that blocks radiation from the laser beam and which comprises a blocking member that has a dimension between 1 and 3 mm.

17. A process according to claim 1 wherein the laser beam is directed against a cap shaped member having a diameter between 1 and 3 mm and which has a concave under surface designed to be positioned over a central portion of the eye.

18. A process according to claim 17 wherein said ablating an annular portion includes adjusting a diameter control system of a laser beam generating device which control system is specifically set up to provide a range of laser beam diameters that extend within a range greater than 1 mm to an upper limit of about 3.5 mm, so as to form an annular ring in the eye having a width defined by an external diameter of said cap and the diameter of said laser beam.

19. A process according to claim 1 wherein said ablating an annular portion includes adjusting a diameter control system and positioning system of a laser beam generating device, which diameter control system is specifically set up to form a range of annular ring ablations having an inner diameter of 1–3 mm and an outer diameter suited for correcting presbyopia of the eye.

20. A system for surgically correcting presbyopia comprising:
    means for resecting at least a portion of a cornea of the eye of the patient to expose a corneal stroma; and
    means for ablating an annular portion of the corneal stroma including a laser, wherein ablation takes place by irradiating the corneal stroma with radiation from the laser, and wherein
    the means for ablating includes means for leaving an unablated central optic zone with a diameter in the range of 1–3 millimeters, and for providing an effective presbyopia correcting width and depth configuration, with the effective presbyopia correcting width having an outer diameter of not more than 3.5 millimeters.

21. A system according to claim 20, wherein the means for resecting includes a corneal shaper which partially resects the cornea such that a portion of the cornea remains intact.

22. A system according to claim 20, wherein the means for resecting includes a corneal shaper which completely removes a disk of the cornea to thereby expose the corneal stroma.

23. A system according to claim 20, further including means for drying the corneal stroma after it has been exposed by the means for resecting.

24. A system according to claim 20, wherein the laser is a pulsed laser.

25. A system according to claim 20, further including means for cleaning the portion which was ablated.

26. A system according to claim 25, wherein the means for cleaning includes a brush and means for irrigating the portion which was ablated.

27. A system as recited in claim 20, further comprising marking means for marking a presbyopia correction ablation ring having an interior diameter of about 1–3 mm.

28. A system for surgically correcting presbyopia comprising:
    means for resecting at least a portion of a cornea of the eye of the patient to expose a corneal stroma; and
    means for ablating an annular portion of the corneal stroma including a laser, wherein ablation takes place by irradiating the corneal stroma with radiation from the laser and wherein the means for ablating leaves the unablated central optic zone with a diameter in the range of about 1–3 millimeters: and
    wherein the means for ablating includes a mask which is positioned over a central area of the corneal stroma to absorb radiation from the laser, and means for providing a predetermined diameter to a laser beam from the laser, such that an annular ablation of a predetermined width and depth for correcting presbyopia is provided in conjunction with the mask.

29. A system according to claim 28, wherein the mask is made from polymethyl methacrylate.

30. A process for surgically correcting presbyopia, comprising:
    resecting at least a portion of a cornea of an eye of a patient to expose a corneal stroma;
    ablating an annular portion of the corneal stroma using radiation from a laser beam, wherein during the ablating step, a central optic zone of the corneal stroma is having a diameter in the range of 1 to 3 millimeter is left unablated; and
    repositioning the portion of the cornea onto the eyes wherein a central corneal curvature change is induced to thereby correct presbyopia in the patient.

31. A process for surgically correcting presbyopia according to claim 30, wherein the annular portion which is ablated has an outer diameter not exceeding 3.5 millimeters.

32. A process as recited in claim 30, wherein said annular ablation is formed on an eye having a distinct eye correction ablation selected from a group consisting of a hyperopia, myopia and an astigmatism eye correction procedure.

33. A system for surgically correcting presbyopia, comprising:
    a laser system which outputs a laser beam with sufficient energy for ablation of an eye, said laser system including a directing system for directing the laser beam at the corneal stroma of the eye; and
    means for controlling the effect of the laser beam with respect to the corneal stroma such that the ablating leaves an unablated central optic zone having a diameter in the range of about 1–3 mm and a presbyopia correcting ablation portion having an effective presbyopia correcting depth and outer periphery configuration of not more than 3.5 millimeters.

34. A system as recited in claim 33 wherein said means for controlling the effect of the laser beam includes a mask member which has a blocking member with a diameter of 1–3 mm so as to block radiation from the laser beam such that there is left the unablated central optic zone having a diameter of 1–3 mm.

35. A system as recited in claim 34 wherein said mask is a cap shaped member having a concave undersurface which conforms to a central curvature of the eye, and said mask having an external diameter of 1–3 mm.

36. A system as recited in claim 34 wherein said means for controlling includes a diameter control system which is specifically set up to provide a range of laser beam diameters that extend within a range greater than a diameter of said blocking member to an upper limit at said effective presbyopia correcting depth and outer periphery configuration, so as to form an annular ring in the eye having a width defined by an external diameter of said cap and the diameter of said laser beam.

37. A system as recited in claim 33 wherein said means for controlling the effect includes a diameter control system and positioning system of the laser system which diameter control system is specifically set up to form a range of circular ring ablations which together define an inner diameter of 1–3 mm and a presbyopia correcting outer diameter and depth configuration.

38. A system as recited in claim 33 further comprising means for resecting at least a portion of a cornea of the eye of the patient to expose a corneal stroma.

39. A process for surgically correcting presbyopia, comprising ablating an annular portion of a cornmeal stroma of a patient with a system that includes a laser system which outputs a laser beam with sufficient energy for ablation of an eye, said laser system including a directing system for directing the laser beam at the corneal stroma of the eye; and means for controlling the effect of the laser beam with respect to the corneal stroma such that the ablating leaves an unablated central optic zone having a diameter in the range of about 1–3 mm.

40. A system for surgically correcting presbyopia, comprising:

a laser system which outputs a laser beam with sufficient energy for ablation of the eye, said laser system including a directing system for directing the laser beam at the corneal stroma of the eye; and means for controlling the effect of the laser beam with respect to the corneal stroma such that the ablating leaves an unablated central optic zone having a diameter of about 1 millimeters, and for providing a presbyopia correcting width and depth configuration.

* * * * *